(12) United States Patent
Brammer et al.

(10) Patent No.: US 8,687,278 B2
(45) Date of Patent: Apr. 1, 2014

(54) OPTO-MECHANICAL SWITCH

(75) Inventors: Marko Brammer, Karlsruhe (DE);
Timo Mappes, Karlsruhe (DE)

(73) Assignees: Buerkert Werke GmbH, Ingelfingen (DE); Karlsruher Institut fuer Technologie, Karlsruhe (DE)

( * ) Notice: Subject to any disclaimer, the term of this patent is extended or adjusted under 35 U.S.C. 154(b) by 110 days.

(21) Appl. No.: 13/102,107

(22) Filed: May 6, 2011

(65) Prior Publication Data

US 2011/0273703 A1  Nov. 10, 2011

(30) Foreign Application Priority Data

May 7, 2010 (DE) .................... 20 2010 006 536 U

(51) Int. Cl.
*G02B 27/14* (2006.01)
*G02B 26/10* (2006.01)
*G02B 6/26* (2006.01)

(52) U.S. Cl.
USPC .............. 359/637; 359/209.1; 359/211.1; 359/813; 385/16; 385/18; 385/19; 385/25; 385/42; 385/47

(58) Field of Classification Search
USPC ........... 359/196, 197, 209, 211, 637; 356/69, 356/72; 385/13, 15–18, 20, 21, 25, 27, 33, 385/36, 39–42, 47, 48
See application file for complete search history.

(56) References Cited

U.S. PATENT DOCUMENTS

| | | | | |
|---|---|---|---|---|
| 5,000,534 A | * | 3/1991 | Watanabe et al. | 385/18 |
| 5,594,820 A | * | 1/1997 | Garel-Jones et al. | 385/22 |
| 5,923,798 A | * | 7/1999 | Aksyuk et al. | 385/19 |
| 5,943,454 A | * | 8/1999 | Aksyuk et al. | 385/22 |
| 5,960,132 A | * | 9/1999 | Lin | 385/18 |
| 6,108,466 A | * | 8/2000 | Aksyuk et al. | 385/19 |
| 6,445,842 B1 | * | 9/2002 | Dhuler et al. | 385/17 |
| 6,807,334 B2 | | 10/2004 | Schroeder et al. | |
| 6,819,826 B2 | * | 11/2004 | Chang et al. | 385/18 |
| 6,829,404 B2 | * | 12/2004 | Sugiyama et al. | 385/20 |
| 7,062,119 B2 | * | 6/2006 | Togawa et al. | 385/16 |
| 7,103,243 B2 | * | 9/2006 | Norimatsu | 385/18 |
| 7,215,853 B2 | * | 5/2007 | Morita et al. | 385/47 |
| 7,973,373 B2 | * | 7/2011 | Mori et al. | 257/414 |
| 2003/0086823 A1 | | 5/2003 | Fernando | |
| 2006/0159388 A1 | | 7/2006 | Kawase | |
| 2007/0230867 A1 | | 10/2007 | Chen et al. | |

FOREIGN PATENT DOCUMENTS

| | | |
|---|---|---|
| DE | 4228733 | 3/1994 |
| WO | 0225352 | 3/2002 |

OTHER PUBLICATIONS

German Search Report dated Mar. 16, 2011.

\* cited by examiner

*Primary Examiner* — Loha Ben
(74) *Attorney, Agent, or Firm* — Carlson, Gaskey & Olds, PC

(57) ABSTRACT

An opto-mechanical switch produces different optical paths from two optical path sections out of a plurality of optical path sections that are oriented in different spatial directions. The switch has an optical component on which one end of each optical path section impinges, and which is adapted to be moved linearly in a direction of movement at right angles to the optical path sections between different switching positions, in which it selectively couples different optical path sections optically with each other. Further provided is a measuring system for the analysis of fluids, having such an opto-mechanical switch.

18 Claims, 4 Drawing Sheets

OPTO-MECHANICAL SWITCH

RELATED APPLICATION

This application claims priority to German Application No. 20 2010 006 536.4, which was filed 7 May 2010.

FIELD OF THE INVENTION

The invention relates to an opto-mechanical switch and to a measuring system for the analysis of fluids, including this opto-mechanical switch.

BACKGROUND

Various optical devices are known which have, for example, adjustable, in particular rotatable, optical elements such as minors, and which serve to couple light guided through an optical fiber into a second or a further optical fiber from a plurality of possible other optical fibers. Usually, all optical path sections to be connected with each other lie in a common plane.

It is the object of the invention to provide a compact opto-mechanical switch which optically connects optical path sections with each other that lie in the same plane or in different planes, and which is therefore very flexible.

SUMMARY

For producing different optical paths from two optical path sections out of a plurality of optical path sections, the opto-mechanical switch includes an optical component on which one end of each optical path section impinges. The optical component is positioned at right angles to the optical path sections and is linearly displaceable in a direction of movement between different switching positions. Two respective optical path sections out of a plurality of optical path sections that are oriented in different spatial directions are selectively coupled optically with each other.

Advantageously, at least three switching positions of the optical component are provided and each switching position of the opto-mechanical switch has a discrete position of the optical component in the direction of movement assigned to it. The optical path sections impinge on different portions of the optical component at different positions in the direction of movement in the different switching positions and the different portions include optical functional elements which each bring about an optical function such as transmission or reflection, between the optical path sections connected with each other. More particularly, in each switching position, light guided by a first optical path section is guided on in a selected second optical path section, based on the position of the optical component.

The optical component advantageously includes a plurality of differently configured portions with optical functional elements that are arranged one on top of the other in the direction of the linear movement of the optical component. Transparent bodies such as lenses, prisms, or diffractive optical elements (DOE), with or without at least partly metal-coated surfaces come into consideration for use as functional elements. Owing to their flat structural shape, Fresnel lenses are also particularly suitable. If it is intended to select specific wavelengths, gratings or prisms are used. In this way, it is also possible to split up and further conduct a plurality of beams. In the opto-mechanical switch, each switching position is assigned one of the portions that can be selectively addressed.

In the opto-mechanical switch, preferably at least two optical path sections lie in a first plane, the first plane extending perpendicularly to the direction of movement of the optical component. In particular, the two optical path sections may be opposite each other in the first plane. Via the optical component, the first optical path section is in this way guided on linearly by the second optical path section lying opposite to it, thus constituting an extension for the first optical path section.

In a further embodiment, in the opto-mechanical switch at least four optical path sections are arranged in a cross shape in the first plane, preferably at an angle of 90 degrees in relation to each other. In this way, light from a first optical path section can be coupled into a second optical path section disposed to the left or right of the first one. The angle may, of course, also assume any desired value other than 90 degrees and may be suited to the specific environment and application, depending on the geometric installation situation of the opto-mechanical switch.

At least one further optical path section may be arranged in a second plane which is perpendicular to the first plane in the opto-mechanical switch and intersects the optical component. Light guided in a first optical path section that is disposed at right angles to the optical component can in this way be coupled into a further optical path section in the direction of the linear movement of the optical component. This has the advantage that light can be transferred not only within a two-dimensional area, but also in a three-dimensional network that is formed of a multitude of optical path sections.

The portions of the optical component that are formed as optical functional elements advantageously have a square base and are preferably formed in a cube shape, at least one portion being formed as a transparent body for the transmission of light and optically coupling opposite optical path sections with each other, and/or at least one portion being formed to have a reflective surface, in particular a mirror surface, for the reflection of light and optically coupling optical path sections with each other that are arranged at an angle to each other, the optical component preferably including at least two portions for reflection which include reflecting surfaces located one above the other in the direction of movement and together forming an angle, in particular of 90 degrees. The square base and in particular the cube shape has the advantage that, owing to the high symmetry, the ends of the optical path sections can all be guided toward the optical component in an identical manner, and coupling light into and out of the planar, oppositely parallel side faces can be realized in a simple manner.

Light guided in a first optical path section can arrive into a second optical path section via the transmission portion of the optical component. In this connection, it is particularly advantageous that this process is bidirectional. The optical component is of such a design that all optical path sections are equally suitable for coupling light in or out.

The portion for the reflection of light includes reflective surfaces, such as, for example, minors or metal-coated surfaces, for use as reflecting means. The metal-coated surfaces may be metal-coated hypotenuse faces of triangular prisms, for example.

Preferably, a portion of the optical component includes a reflective surface which is formed by metal-coated hypotenuse faces of two triangular prisms assembled at these faces, the hypotenuse faces being arranged at an angle of 45 degrees and 135 degrees relative to first and second optical path sections, respectively, which are perpendicular to each other, and the portion of the optical component optically coupling the first optical path section with the second optical path section. This allows a design in which two prisms each are assembled at their hypotenuse faces such that they form a cube or at least a cuboid having a square base which expediently has the same dimensions as the side faces of the transmission cube. The reflection cube is connected on one side face with the transmission cube to fully cover one side face thereof, so that the metal-coated hypotenuse faces are positioned perpendicular to the interconnected side faces.

When light from a first optical path section end impinges on the optical component within one of its reflective portions, it is reflected on the minor surface and, depending on the angle of incidence, is deflected accordingly to a second optical path section. Preferably, light is deflected at an angle of 90 degrees and is then coupled into a second optical path section end, which likewise forms an angle of 90 degrees with the first optical path section end. Coupling light in or out works in both directions in the reflective portion of the optical component as well.

As many reflective portions as desired may be arranged on top of each other in the optical component in the direction of its linear movement, the reflective surfaces of the reflective portions being arranged at different angles with respect to a first optical path section. In this way, light is coupled into respective second optical path sections, which are disposed at corresponding angles relative to the first optical path section.

In one example embodiment, the reflective surfaces of two reflective portions form a right angle, so that light from a first optical path section is coupled into optical path sections which are orthogonal to the first optical path section, oppositely directed, and jointly arranged in the first plane.

It is of particular advantage that in the respective switching positions, the optical path sections and the portions of the optical component and, hence, all of the optical functional elements as well are fixed relative to each other in a defined spatial arrangement, which is maintained upon a vertical movement of the optical component from one switching position to the next. Thus, one single adjustment process, namely the alignment of the optical component within the opto-mechanical switch, causes all parts to be positioned in relation to each other so as to be ready for operation.

The number of optical path sections that can be coupled with one another can be increased if the optical path sections lie not only in planes perpendicular to the direction of movement of the optical component, but also in the direction of movement. As a result, the optical path sections are oriented in three dimensions. This is achieved in that the optical component has a portion for the reflection of light which couples at least one optical path section extending sideways relative to the direction of movement and an optical path section extending in the direction of movement with each other.

In a further embodiment, the optical component includes a portion for the reflection of light which is formed as a pyramid having metal-coated triangular surfaces. This portion allows an optical coupling of optical path sections that are perpendicular to each other. The pyramid constitutes the termination of the optical component in respect of the extent thereof in the direction of its linear movement on one or both sides. The square base of the pyramid is thus adjacent to a side face of the optical component with a transmission or reflection portion. When light from one of the optical path sections which lie in a plane parallel to side faces connecting the portions with each other impinges on a metal-coated triangular surface of the pyramid, the light is deflected in a direction perpendicular to these optical path sections corresponding to the direction of linear movement of the optical component and coupled into optical path sections provided therefor. The opto-mechanical switch thereby connects horizontal and vertical optical path sections with each other. Advantageously, in this case too, a bidirectional light conduction is possible through optical path sections optically connected with each other.

A precise change in position of the optical component may be attained in that the optical component is coupled to a linear motor, preferably a spindle drive. In particular, the optical component includes a holder, preferably a pedestal, which is coupled to the linear motor, in particular with a spindle. The holder may be configured as a cuboid body, for example, which is arranged on the side of the optical component. But it is also possible to connect the lower side of the optical component with a pedestal which, for its part, cooperates with the linear motor with a fastening mechanism such as a spindle.

If the holder is mounted to a side of the optical component, a possible light deflection or transfer direction may not be usable. The mounting of the holder to the optical component expediently requires only one single side face, so that all other side faces in the opto-mechanical switch remain free for ends of optical path sections to be able to impinge there.

Via the linear motor, one of the portions of the optical component is selectively addressable. Optical path sections are thereby optically connected with each other in the opto-mechanical switch which all lie in the first plane, or an optical path section in the first plane is optically connected with an optical path section in a plane perpendicular thereto.

Preferably, a housing is provided in which the optical component and the linear motor are arranged, the housing allowing an adjustment of the optical component, preferably by a unit made up of the optical component and the linear motor being rotatably arranged in the housing. This allows a simple adjustment of the optical component.

Advantageously, the housing is configured to accommodate the optical path sections, the optical path sections and the portions of the optical component being fixed relative to each other in a defined spatial arrangement in the respective switching positions. In this way, no separate adjustment of the optical path sections in relation to each other is necessary since the positioning thereof is specified by the housing.

To achieve a good and well-defined conduction of the light, the optical path sections may be formed by optical fiber ends.

In order to allow complex optical functions, the optical component may include a portion which is configured as an optical functional element and includes one or more of the following optical elements: diffractive optical elements, in particular diffraction gratings, refractive optical elements, in particular lenses or prisms, polarization elements and/or beam splitters.

The optical switch may be advantageously utilized for diverting and/or further conducting light in a three-dimensional space and is excellently suited for a measuring system for the analysis of fluids in which fluid properties are determined which are based on an optical measuring principle such as, for example, absorption, transmission, turbidity or fluorescence, a plurality of measuring stations being arranged in the measuring system side by side and on top of each other. Selected measuring stations are fluidically driven by valves and pumps, and optically addressed in that optical path sections are selectively coupled with each other of the opto-mechanical switch. The optical switch is especially suitable for use in miniaturized optical analysis systems.

Example embodiments of the switch have dimensions of approx. 20 mm×10 mm×10 mm; substantially smaller embodiments are, however, also realizable, e.g., 10 mm×5 mm×5 mm.

These and other features of the present invention can be best understood from the following specification and drawings, of which the following is a brief description.

DETAILED DESCRIPTION

Figure 1:
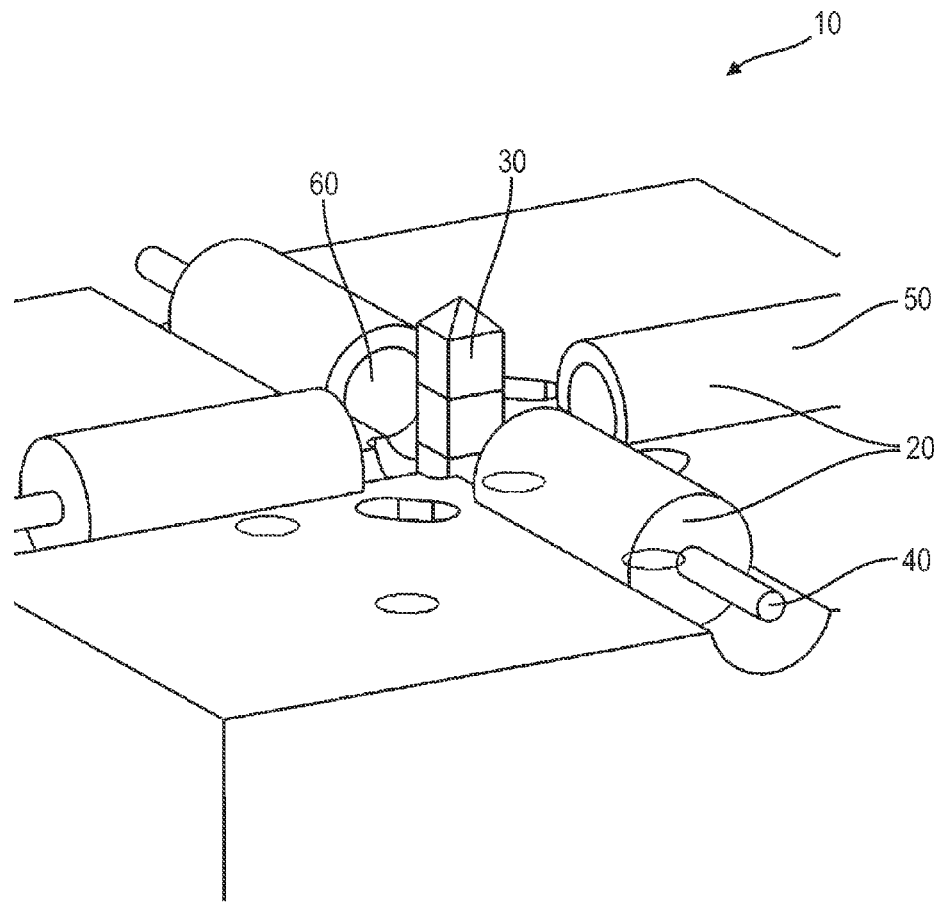
FIG. 1 shows a spatial illustration of an embodiment of an optical switch.

FIG. 1 illustrates an opto-mechanical switch 10 including a plurality of optical path sections 20, which are oriented in different spatial directions, and an optical component 30 on which the inner ends of the optical path sections 20 impinge. The optical component 30 is linearly movable at right angles to the optical path sections 20 between different switching positions. The different switching positions allow a selection to be made as to which optical path sections 20 are optically coupled with each other.

In the embodiment shown, four optical path sections 20 are arranged in a common first plane. The direction of movement of the optical component 30 is perpendicular to the first plane.

According to the embodiment shown in FIG. 1, the ends of the optical path sections 20 are configured as ends of optical fibers 40, which are guided in holders 50. This has the advantage that a desired geometric arrangement of the optical path sections 20 relative to each other and to the optical component 30 can be fixed in place in a simple way while stabilizing the optical fibers 40 at the same time. Optical parts for beam focusing, such as lenses 60, can be inserted into the holders 50 across from the optical component 30.

The optical path sections 20 may, however, also be other light-conducting bodies which are made from a transparent material such as glass or plastic, and/or include free optical paths lengths. Advantageously, the free optical paths lengths are minimal to reduce a widening of the beam.

Two optical path sections 20 each are arranged opposite one another in the first plane. With this simple arrangement, light that has been coupled into a first optical path section by a light source can be guided on in the opposite optical path section. The direction does not play a part here: it may be freely selected into which one of the two oppositely arranged optical path sections light is coupled and in which one the light is passed on.

The embodiment according to FIG. 1 includes four optical path sections 20, which are arranged at right angles to each other and like a cross in a horizontally oriented first plane. The optical component 30 is arranged perpendicularly thereto in the point of intersection of the cross.

The optical path sections 20 are thus arranged in a cross shape in the first plane, two optical path sections 20 each lying opposite each other in the first plane. In the embodiment shown, the angles between neighboring optical path sections 20 each amount to 90 degrees.

The arrangement of the opto-mechanical switch allows light from any desired optical path section 20 lying in the first plane to be coupled into any other optical path section 20 in that the light is selectively guided straight on or appropriately diverted in the optical component.

The beam direction between all optical path sections 20 lying in the first plane is reversible.

In a further embodiment, at least two optical path sections 20 are arranged at any desired angle relative to each other. The optical component 30 diverts light arriving from one optical path section such that it is guided on in the second optical path section.

Furthermore, at least one further optical path section 20 may be arranged above or below the optical component 30 on the vertical axis thereof, which runs through the intersection point of the cross. Using this structure, light arriving from one optical path section 20 can be guided on in one of a plurality of possible spatial directions: it can be diverted to the right, left, upward or downward, or else be guided straight on in an opposite optical path section. As a result, the opto-mechanical switch attains a high flexibility and versatility for application.

The possible light beam paths 70 (symbolized by dashed arrows), proceeding from one optical path section 20 and diverted or guided on by the optical component 30, are schematically illustrated in FIGS. 2a through 2e.

The optical component 30 according to FIGS. 2a through 2e includes a plurality of different portions 80, 90, 100 and 110 having optical functional elements. These different portions 80, 90, 100 and 110 are arranged vertically on top of each other. In each switching position, one respective portion having at least one optical functional element is situated at the level of the first plane, that is, at the point of intersection of the optical path sections. Upon a linear vertical movement of the optical component 30, these portions can thus be addressed one after the other or in any desired order. A linear motor is sufficient for moving the optical component between its different switching positions.

The diversion or further conduction of the light is achieved by transmission, reflection or refraction in an optical functional element of the optical component.

In the case of a cross-shaped arrangement of the optical path sections 20 according to the embodiment shown in FIG. 1, an optical path section 20 can be optically coupled with any of the other optical path sections by simple optical functional elements of the optical component, which each allow a further conduction or diversion of the light beam in the optical component 30.

In the embodiment shown, the linear further conduction is effected by transmission and the diversion is effected by reflection in the respective portions of the optical component.

The optical coupling of two optical path sections is maintained if the beam direction in the opto-electronic switch is reversed.

It is also possible to perform complex optical functions with the opto-mechanical switch in that the optical component comprises a portion which is configured as an optical functional element and which includes one or more of the following optical elements: diffractive optical elements, in particular diffraction gratings, refractive optical elements, in particular lenses or prisms, polarization elements and/or beam splitters.

Provision may also be made for optical functional elements, for example beam splitters, diffractive or refractive optical elements, in which the coupling of two optical path sections is specified only for one predefined beam direction.

The embodiment of the optical component 30 shown in FIGS. 2a through 2d has a square base that is oriented perpendicularly to the direction of movement of the optical component. The optical component includes five portions 80, 90, 100 and 110 having different optical functional elements.

Respective pyramidal portions 110 having metal-coated side faces are formed on the outer ends of the optical component 30 in the direction of movement, which is illustrated to be vertical in each of FIGS. 2a through 2d.

The optical component 30 further includes three cube-shaped portions 80, 90, 100. The side faces of the cubes extend perpendicularly to the optical axis of the respectively assigned optical path sections.

The symmetry of the portions having the square base or of the cube shape ensures that the optical path lengths in the interior of the optical component are substantially identical for the different spatial directions.

In this way, a high quality of the light beam conducted through the opto-mechanical switch can be achieved, in particular with respect to the intensity distribution or the beam shape. As a result, the opto-mechanical switch is particularly suitable for spectroscopic applications.

The portion 80 is configured as a transparent cube and serves for transmission. When light impinges on a side face of this cube, it is conducted through the cube without diversion. This means that in a switching position in which the ends of optical path sections impinge on the portion 80, opposite optical path sections are optically coupled with each other. The free beam path is very small here, which is beneficial to a low-loss light conduction. In the exemplary embodiment, four optical path sections 20 lying in a horizontal plane impinge on side faces of the cube.

It is, however, also possible to position the optical component 30 in one switching position such that the optical component 30 is situated below the light beam which, arriving from one optical path section, falls into the opposite one unhindered. This variant is likewise shown in FIG. 2a.

Figure 2A:
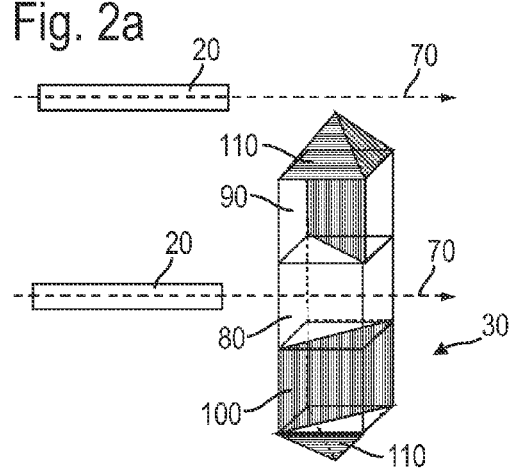
FIG. 2a shows the light diversion or further conduction in an embodiment of the optical component.
Figure 2B:
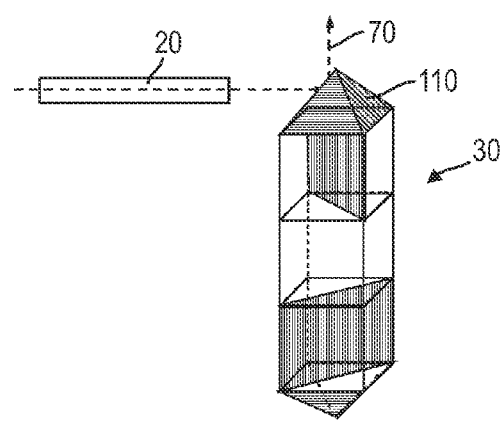
FIG. 2b shows the light diversion or further conduction in an embodiment of the optical component.
Figure 2C:
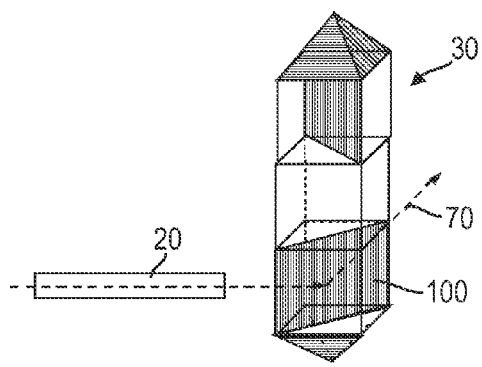
FIG. 2c shows the light diversion or further conduction in an embodiment of the optical component.
Figure 2D:
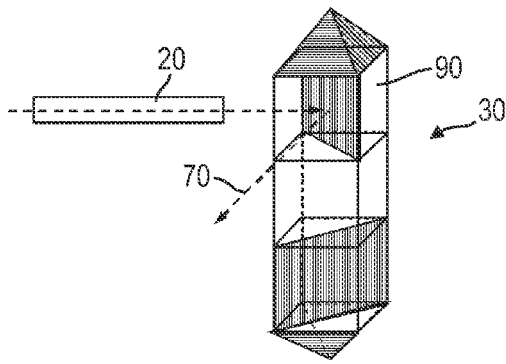
FIG. 2d shows the light diversion or further conduction in an embodiment of the optical component.
Figure 2E:
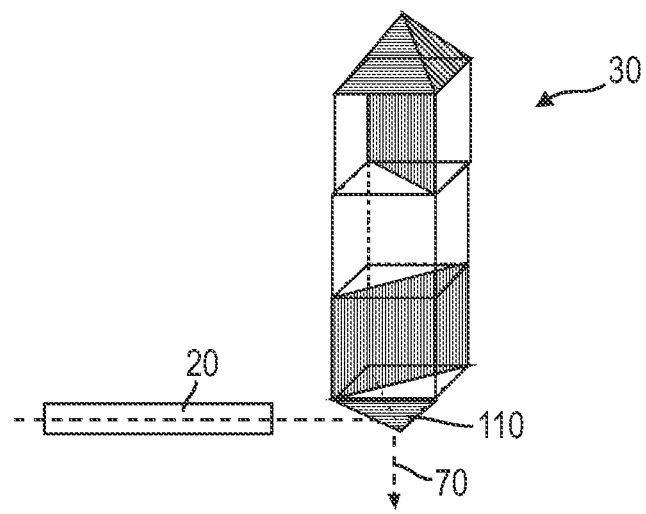
FIG. 2e shows the light diversion or further conduction in an embodiment of the optical component.

FIGS. 2b and 2e illustrate how light from a horizontal plane is diverted upward (2b) or downward (2e) into a vertical plane in the portions 110 of the optical component 30. The portion 110 is in the form of a pyramid having a square base and metal-coated triangular side faces. Light impinging on the metal-coated side faces is reflected thereon. Angles of deflection other than that of 90 degrees as illustrated here are also possible. The size of the angle of deflection depends on the angle of inclination of the side faces in relation to the pyramid base and the point of impingement of the incident light. In the associated switching position, all four optical path sections 20 lying in a horizontal plane impinge on the triangular side faces of the pyramid, and light guided therein is deflected upwards or downwards.

The portions 110 are suitable as terminations of the optical component 30 and are connected at their bases with a respective outer side face of another portion.

The portions 90 and 100 also serve for the reflection of light. Here, however, the light is deflected within the horizontal plane, as is illustrated in FIGS. 2c and 2d. A reflecting cube is assembled from two transparent triangular prisms at the hypotenuse faces thereof. The hypotenuse faces are metal-coated, so that light impinging there is deflected, following the law "angle of incidence equals angle of reflection". In the embodiment shown, the reflecting cube is oriented such that light from a first optical path section 20 is diverted into a second optical path section 20 disposed perpendicularly thereto. The optical path sections 20 are disposed at an angle of 45 degrees and 135 degrees, respectively, in relation to the reflecting surface. FIGS. 2c and 2d show a deflection to the left and to the right, respectively. The hypotenuse faces of the portions 90 and 100 of the two reflecting cubes are also arranged at an angle of 90 degrees relative to each other and are perpendicular to the plane in which the optical path sections to be optically coupled with each other are disposed.

In both cases, 2c and 2d, in the associated switching positions, four optical path sections 20 lying in the horizontal plane each terminate at two respective side faces of the two assembled triangular prisms, and both hypotenuse faces reflect light that is incident there.

Depending on the orientation of a reflecting cube and, hence, of the reflecting surface, relative to a first optical path section, any desired angles of deflection other than 90 degrees can be set, the geometric position of the second optical path section then being adjusted thereto accordingly.

An optical component 30 may be provided with any desired number of optical portions that include optical functional elements. Here, a plurality of reflecting cubes and transmission cubes may be arranged vertically on top of each other in any desired order, with the outer side faces thereof being adapted to have a reflecting pyramid as a termination on one or both sides along the vertical axis.

Three switching positions of the optical component are sufficient for coupling the four optical path sections lying in the first plane, each switching position being assigned a discrete position of the optical component in the direction of movement, the optical path sections impinging on the three cube-shaped portions 80, 90, 100 of the optical component in the different switching positions, each of the three switching positions coupling two respective ones of the optical path sections with each other.

Figure 3:
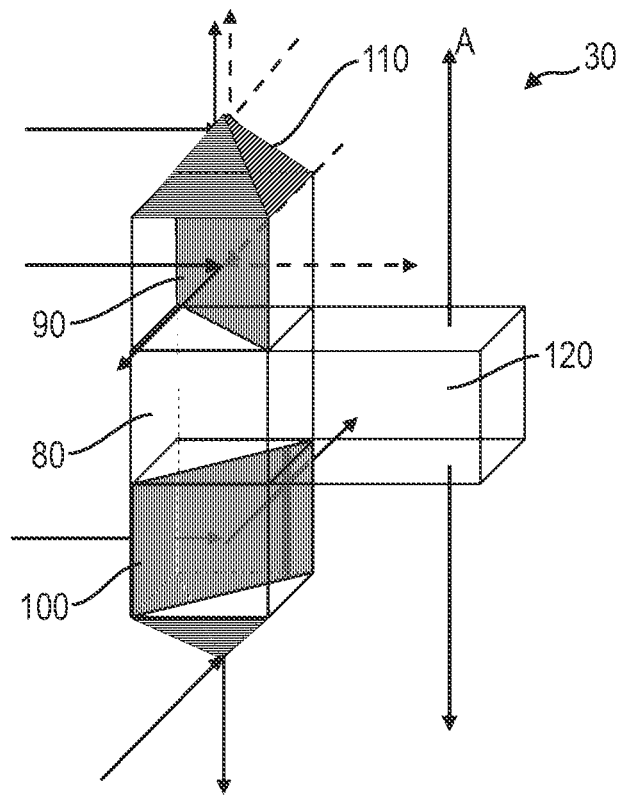
FIG. 3 shows an embodiment of an optical component with a holder.

FIG. 3 shows an embodiment of an optical component 30 having a holder 120. The holder 120 is of a cuboid configuration and is firmly connected to the optical component 30 on one side face thereof. The holder 120 is moved along the axis A by a linear motor and, thus, the optical component 30 is moved along its vertical axis, which extends parallel thereto. Possible optical paths in the various switching positions are illustrated by arrows, as already described in detail for FIGS. 2a through 2e; it should be appreciated here that, for the sake of clarity, not all possible light paths are shown.

Figure 4:
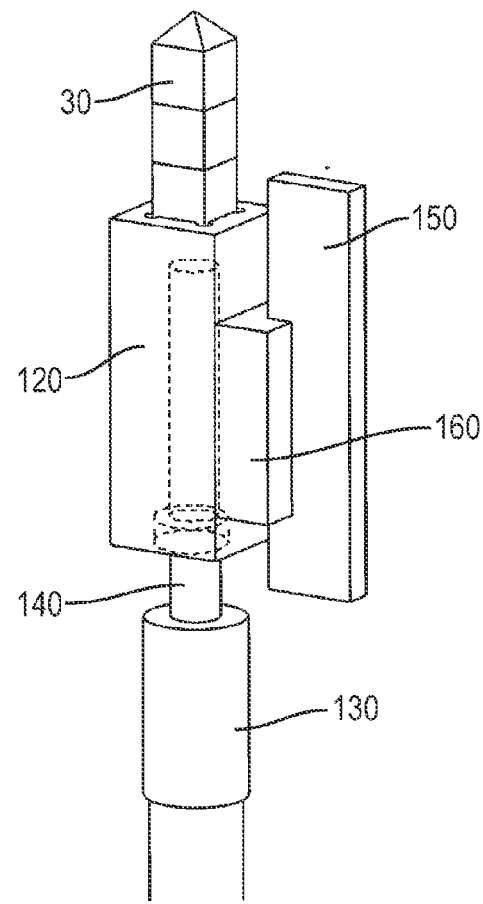
FIG. 4 shows a further embodiment of an optical component with a holding means and a linear motor.

FIG. 4 illustrates a further embodiment of an optical component 30 having a holder 120. The holder 120 is in the form of a pedestal having the optical component 30 placed on its top side and firmly connected to it. A linear motor 130 is arranged on the oppositely located bottom side of the holder 120 and is connected with the holder with a spindle 140. The spindle 140 is driven by the linear motor 130.

A spindle drive of this type allows a precise positioning of the optical component in a multitude of switching positions along the direction of movement of the optical component. The number of switching positions preferably corresponds to the number of the different portions of the optical component and may additionally include a position in which the optical component has been completely moved out of the point of intersection of the optical path sections.

An especially precise positioning of the optical component may be obtained for functional elements which are outermost in the direction of movement if the optical component or the holding means rests against a stop in this position. This more particularly allows a precise reflection of a light beam on the reflecting pyramid having reflective side faces that are oblique to the direction of movement.

In this embodiment, the optical component 30 includes a reflecting pyramid only on its upper terminating side. Opposite to the upper terminating side, a planar cube side face on the lower side of the optical component 30 is expediently firmly connected with the holder 120. A rail 150 and a slider 160 are provided for guidance.

Figure 5:
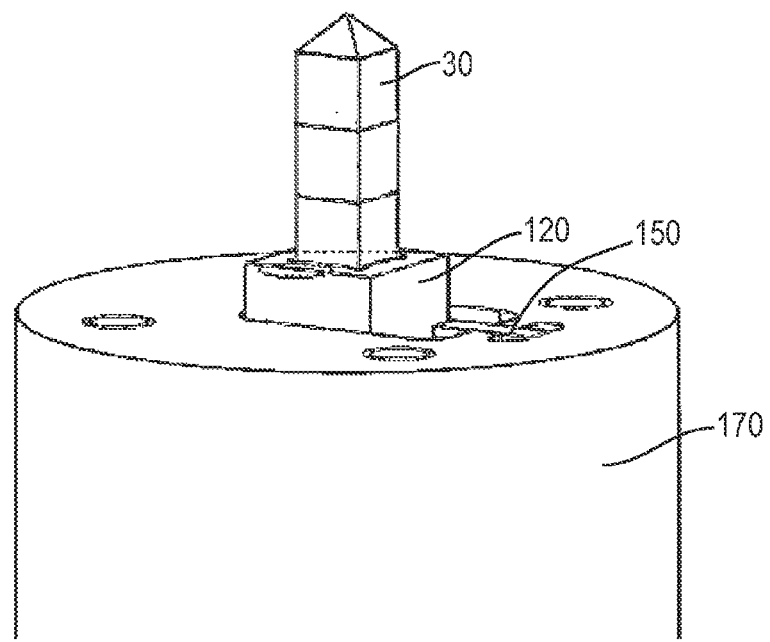
FIG. 5 shows an embodiment according to FIG. 4 with a housing.

FIG. 5 illustrates an embodiment of the optical component 30 which includes the holder 120 and the rail 150 according to FIG. 4 as well as a housing 170. The linear motor 130 is also arranged in the housing 170. The housing 170 is inserted in the opto-mechanical switch 10 according to FIG. 1. The adjustment of the optical component 30 takes place there, that is, its alignment in relation to the optical path sections 20, which is then maintained in all switching positions.

The optical component and the linear motor constitute an assembly which is arranged for rotation in the housing and thus allows a simple adjustment. In this way, the optical component may be oriented in relation to the optical path sections arranged in the housing.

Owing to its high flexibility, the opto-mechanical switch 10 is suitable for an analyzing measuring system in which optical properties of fluids are to be detected. The analysis system is fitted with valves, pumps, mixing chambers for mixing the fluids with reagents, and fluid ducts leading to measuring stations including sensors for the detection of, more specifically, transmission, absorption, turbidity or fluorescence. The measuring stations are spatially arranged side by side and on top of each other, so that a complex system having fluid ducts and light paths is produced. Depending on the desired measuring data to be determined by analysis programs, fluids are guided to the appropriate measuring stations in parallel or in succession. The opto-mechanical switch can be used for selectively coupling optical path sections with each other, so that the selected measuring stations are optically addressed.

The opto-mechanical switch is suitable for monochromatic or polychromatic light, with suitable optical functional elements being used depending on the type of light.

Although an embodiment of this invention has been disclosed, a worker of ordinary skill in this art would recognize that certain modifications would come within the scope of this invention. For that reason, the following claims should be studied to determine the true scope and content of this invention.

What is claimed is:

1. An opto-mechanical switch for producing different optical paths from two optical path sections out of a plurality of optical path sections that are oriented in different spatial directions, comprising:
   an optical component on which one end of each optical path section impinges and which is adapted to be moved linearly in a direction of movement at right angles to the optical path sections between different switching positions in which the optical component selectively couples different optical path sections optically with each other; and
   wherein at least three switching positions of the optical component are provided and each switching position has a discrete position of the optical component in the direction of movement assigned to the optical component, the optical path sections impinging on different portions of the optical component at different positions in the direction of movement in the different switching positions, and the different portions including optical functional elements that bring about an optical function between the optical path sections connected with each other, the optical function comprising transmission or reflection.

2. The opto-mechanical switch according to claim 1, wherein at least two optical path sections lie in a first plane, the first plane extending perpendicularly to the direction of movement of the optical component.

3. The opto-mechanical switch according to claim 2, wherein at least four optical path sections are arranged in a cross shape in the first plane at an angle of 90 degrees in relation to each other.

4. The opto-mechanical switch according to claim 2, wherein at least one further optical path section is arranged in a second plane which is perpendicular to the first plane and intersects the optical component.

5. The opto-mechanical switch according to claim 2, wherein the at least two optical path sections lying in the first plane are arranged opposite to each other.

6. The opto-mechanical switch according to claim 1, wherein portions of the optical component that are formed as optical functional elements have a square base, and wherein at least one of these portions is formed as a transparent body for the transmission of light and optically coupling opposite optical path sections with each other.

7. The opto-mechanical switch according to claim 6, wherein the portions of the optical component having a square base are formed in a cube shape.

8. The opto-mechanical switch according to claim 1, wherein at least one portion of the optical component is formed to have a reflective surface for the reflection of light and optically coupling optical path sections with each other that are arranged at an angle to each other.

9. The opto-mechanical switch according to claim 8, wherein the optical component comprises at least two portions for reflection which include reflecting surfaces located one above the other in the direction of movement and together forming an angle of 90 degrees.

10. The opto-mechanical switch according to claim 8, wherein a portion of the optical component includes a reflective surface which is formed by metal-coated hypotenuse faces of two triangular prisms assembled at these faces, the hypotenuse faces being arranged at an angle of 45 degrees and 135 degrees relative to first and second optical path sections, respectively, which are perpendicular to each other, and the portion of the optical component optically coupling the one optical path section with another optical path section.

11. The opto-mechanical switch according to claim 1, wherein the optical component is coupled to a linear motor, and wherein the optical component includes a holder that is coupled to the linear motor with a spindle.

12. The opto-mechanical switch according to claim 11, including a housing in which the optical component and the linear motor are arranged, the housing allowing an adjustment of the optical component, and the linear motor being rotatably arranged in the housing.

13. The opto-mechanical switch according to claim 12, wherein the housing allows an adjustment of the optical component by a unit made up of the optical component.

14. The opto-mechanical switch according to claim 13, wherein the housing is configured to accommodate the optical path sections, the optical path sections and portions of the optical component being fixed relative to each other in a defined spatial arrangement in the respective switching positions.

15. The opto-mechanical switch according to claim 1, wherein the optical path sections are formed by optical fiber ends.

16. The opto-mechanical switch according to claim 1, wherein the optical component comprises a portion which is configured as an optical functional element and includes one or more of the following optical elements: diffractive optical elements, diffraction gratings, refractive optical elements comprising lenses or prisms, polarization elements, beam splitters.

17. An opto-mechanical switch for producing different optical paths from two optical path sections out of a plurality of optical path sections that are oriented in different spatial directions, comprising:
- an optical component on which one end of each optical path section impinges and which is adapted to be moved linearly in a direction of movement at right angles to the optical path sections between different switching positions in which the optical component selectively couples different optical path sections optically with each other; and
- wherein the optical component has a portion for reflection of light which optically couples at least one optical path section extending sideways relative to the direction of movement with an optical path section extending in the direction of movement.

18. An opto-mechanical switch for producing different optical paths from two optical path sections out of a plurality of optical path sections that are oriented in different spatial directions, comprising:
- an optical component on which one end of each optical path section impinges and which is adapted to be moved linearly in a direction of movement at right angles to the optical path sections between different switching positions in which the optical component selectively couples different optical path sections optically with each other; and
- wherein the optical component includes a portion for reflection of light which is formed as a pyramid having metal-coated triangular surfaces and optically couples optical path sections that are perpendicular to each other.

* * * * *